United States Patent [19]

Sundt

[11] 3,979,338

[45] Sept. 7, 1976

[54] 9-[9,12-EPOXY-ETHYL]-4-METHYL TRICYCLO[6.2.1.0$^{2.7}$]UNDEC-4-ENE AND 9-[9,12-EPOXY-ETHYL]-5-METHYL TRICYCLO[6.2.1.0$^{2.7}$]UNDEC-4-ENE ODOUR-MODIFYING AGENTS

[75] Inventor: Erling Sundt, Pinchat-Geneva, Switzerland

[73] Assignee: Firmenich S.A., Geneva, Switzerland

[22] Filed: Dec. 2, 1975

[21] Appl. No.: 637,056

Related U.S. Application Data

[62] Division of Ser. No. 528,669, Dec. 2, 1974, Pat. No. 3,953,534.

[30] Foreign Application Priority Data

Oct. 11, 1971  Switzerland............ 14784/71
May 19, 1972  Switzerland............ 7456/72

[52] U.S. Cl............................ 252/522; 131/17 R; 260/348 C
[51] Int. Cl.$^2$............................ C11B 9/00
[58] Field of Search............ 260/666 PY, 348; 252/522

[56] References Cited

UNITED STATES PATENTS

| 3,489,733 | 1/1970 | Natla et al. | 260/666 PY |
| 3,660,508 | 5/1972 | Dart et al. | 260/666 PY |

OTHER PUBLICATIONS

Abs.–Derwent Netherlands Patents Report, vol. 4, No. 34–Plastics Metal Finishing p. 6, 6702330.

*Primary Examiner*—Veronica O'Keefe
*Attorney, Agent, or Firm*—Pennie & Edmonds

[57] ABSTRACT

Process for the preparation of cycloaliphatic compounds useful as perfuming and odour-modifying agents in the manufacture of perfumes and perfumed products, and as flavoring and taste-modifying agents in the aromatization of foodstuffs in general and imitation flavors for foodstuffs, beverages, animal feeds, pharmaceutical preparations and tobacco products.

Composition of matter relating to some of said cycloaliphatic compounds which are new and perfume- and flavoring compositions containing same.

1 Claim, No Drawings

3,979,338

9-[9,12-EPOXY-ETHYL]-4-METHYL TRICYCLO[6.2.1.0$^{2,7}$]UNDEC-4-ENE AND 9-[9,12-EPOXY-ETHYL]-5-METHYL TRICYCLO[6.2.1.0$^{2,7}$]UNDEC-4-ENE ODOUR-MODIFYING AGENTS

This is a division of application Ser. No. 528,669 filed Dec. 2, 1974, now U.S. Pat. No. 3,953,534.

SUMMARY OF THE INVENTION

The compounds to which the present invention relates belong to the class of tricyclic derivatives having the partial formula

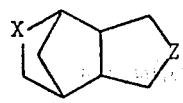

For simplicity in referring to the various compounds of the invention, their derivatives or precursors, the nomenclature used throughout this specification will define the nature of the symbols X and Z by an appropriate combination of letters. This system of nomenclature will be appended to the numbers designating the various formulae given hereinafter.

The invention relates to new cycloaliphatic compounds having the formula

  I wherein the symbol Z represents a radical of formula

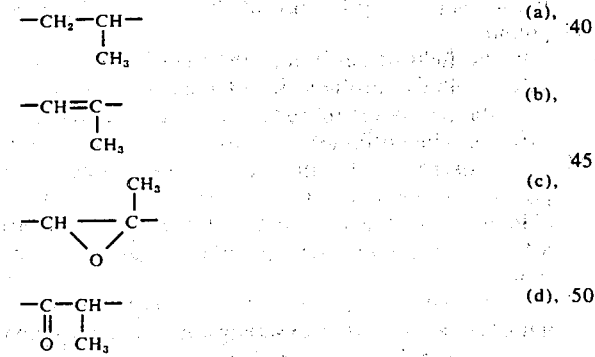

and X represents a divalent radical of formula

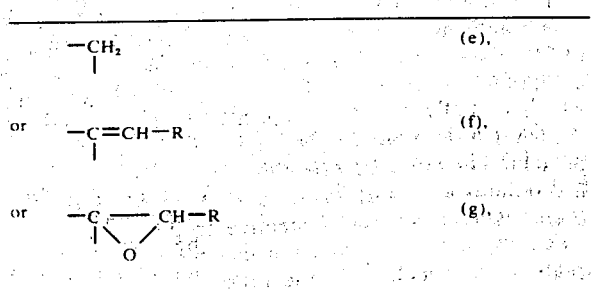

-continued

| | | |
|---|---|---|
| or | —CH—C—R<br>$\quad\ \ $∥<br>$\quad\ \ $O | (h), |
| or | —CH—CH—R<br>$\quad\ \ $$\|$ $\quad$ $\|$<br>$\quad\ \ $OR$^1$ | { i: R$^1$=H<br>{ i′: R$^1$=acyl |
| or | —CH—CH=CH—R | (j), | wherein

R represents a hydrogen atom or an alkyl radical comprising from 1 to 6 carbon atoms, and R$^1$ represents a hydrogen atom or an acyl radical.

The above mentioned compounds possess interesting organoleptic properties and, moreover, may be used as intermediates for the preparation of other compounds having useful fragrant and flavouring properties.

It is a further object of the present invention to provide a process for the preparation of the compounds of formula I, as defined above, which process comprises A. treating isoprene with a compound of formula

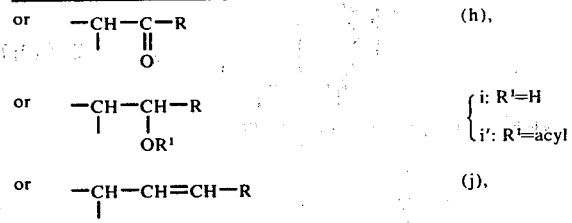  II wherein X has the same meaning as that indicated for formula I, to yield a compound of formula I wherein Z represents a radical of formula

 (b)

or

B. epoxidizing the compounds of formula

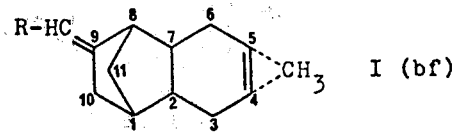  I (bf)

wherein a methyl group is bound to a carbon atom in position 4 or 5, and the symbol R represents a hydrogen atom or an alkyl radical comprising from 1 to 6 carbon atoms, to yield a compound of formula

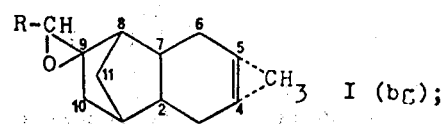  I (b$_C$);

or

C. catalytically hydrogenating a compound of formula

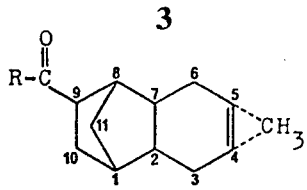

I (bh)

to yield a compound of formula

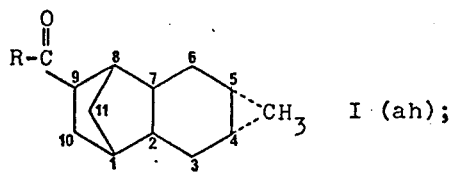

I (ah);

or

D. reducing a compound of formula I (bh) or I (ah), as indicated under letter C., to yield an alcohol of formula

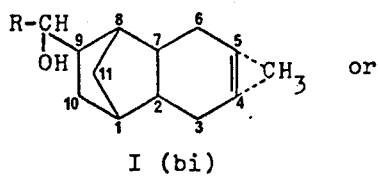

I (bi)

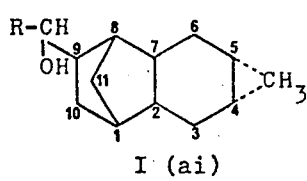

I (ai)

respectively; or

E. esterifying an alcohol of formula I (bi) or I (ai), as indicated under letter D., to yield an ester of formula

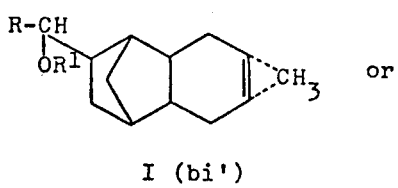

I (bi')

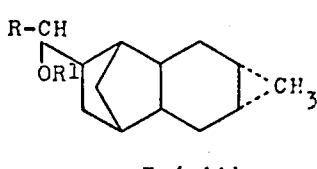

I (ai')

respectively; or

F. epoxidizing a compound of formula

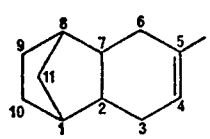

I (be)

to yield an epoxide of formula

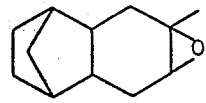

I (ce)

which upon subsequent treatment with an acidic or a basic agent affords a ketone of formula

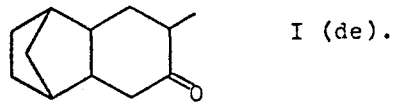

I (de).

BACKGROUND OF THE INVENTION

One of the main objects of the aromatization of foodstuffs for instance is to restore the original quality and nature of the flavour, aroma and taste of a given foodstuff material. Very often in fact the organoleptic properties of foodstuffs particularly diminish or are somehow modified in the course of the processes of freezing and storage, or during the modifications, such as cooking or baking, to which the foodstuffs are subjected in order to yield an edible material.

In the past the aromatization was mainly achieved by using materials of natural origin. Nowadays, however, synthetic chemical compounds are used at an ever increasing rate. Said compounds possess the advantage of being available very often in unlimited quantities and at prices lower than those of the natural materials. Moreover, due to the fact that the flavouring character of a natural material is the result of the overall effect determined by the combination and interaction of each of its constituents, the effects achieved by said natural material are very often not as well reproducible as those obtained by the use of the pure synthetic compounds.

In the field of perfumery the man in the art has to solve a similar problem in attempting to reconstitute the olfactive notes of certain natural essential oils or extracts. The perfumer's creativity however is continually boosted by the finding of new synthetic compounds, the organoleptic properties of which will enable him to introduce unprecedented olfactive characters or nuances into new phantasy perfume compositions.

As a consequence, the problem that the chemical industry has to solve is to satisfy the increasing demand of organoleptically interesting chemicals in order to better suit the specific needs of flavourists and perfumers.

PREFERRED EMBODIMENTS OF THE INVENTION

As mentioned above, according to the invention the compounds of formula I wherein Z represents a radical of formula (b) are prepared by treating isoprene with a compound of formula II. Preferably, the said reaction, which formally may be represented by an addition of the Diels-Alder type, can be carried out in the presence of an inhibitor of polymerization, e.g. in the presence of hydroquinone, pyrogallol or a mixture of these two compounds in different respective proportions.

Equally, the above reaction can be carried out by treating the reactants in the presence of the chosen inhibitor under an atmosphere of an inert gaz, such as e.g. nitrogen or argon. However, this specific operation technique does not bring about any substantial improvement of the total yield of the thus obtained final product.

No particular addition agent is requested. The said addition is however better promoted by the action of heat and, in certain instances, of a pressure higher than the atmospheric pressure. Thus it is preferred to operate at a temperature comprised between about 100° and about 200°C, preferably between 150° and 180°C, and at a pressure comprised between about 10 and 200 atmospheres. The temperature and pressure ranges indicated above may however vary within wide limits and values higher or lower than those indicated may be used.

The compounds of formula II, wherein X represents a radical of formula (e), (f) or (j), used as starting materials for the above mentioned process, are either materials commercially available, or compounds which may be prepared by known synthetic methods [see e.g.: Dutch Pat. application No. 66 13870].

The compounds of formula II, wherein X represents a radical of formula (g), (h), (i) or (i') may be obtained by the subsequent conversion of the corresponding compounds of formula II (e), II (f) or II (j) according to known chemical techniques, such as for instance epoxidation, in order to form the corresponding epoxide derivatives; ring-opening of said epoxide derivatives, in order to form the corresponding ketone derivatives; reduction of said ketone derivatives by means of metal hydrides, to form the corresponding alcohols; and esterification of said alcohols to form the corresponding esters.

In accordance with the process of the invention the compounds of formula I (bg) are obtained by epoxidizing a compound of formula I (bf). Said epoxation can be carried out by means of an organic peracid such as peracetic, perbenzoic, monochloroperbenzoic, perphthalic, performic or trifluoroacetic acid in an inert solvent such as e.g. a chlorinated hydrocarbon, e.g. chloroform, methylene chloride, trichloroethylene or dichloroethane.

Moreover, the epoxidation can be carried out in a buffered medium. Typically, advantageous buffered media include an alkali metal salt of an organic acid, such as e.g. formate, acetate, propionate, butyrate, oxalate, citrate or tartrate of sodium or potassium. Sodium acetate in methylene chloride is preferred.

The temperature at which said epoxidation is carried out may vary within wide limits. However, the best yields of the final products are obtained by carrying out the epoxidation at a temperature of about 0°C or at a lower one, preferably comprised between about 0 and -10°C. At higher temperatures a concomitant formation of a diepoxide of formula I (cg)

wherein a methyl group is bound to a carbon atom in position 4 or 5, and of a monoepoxide of formula

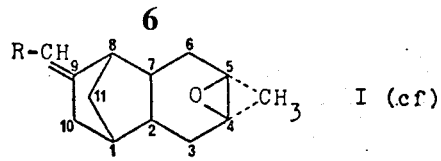

I (cf)

takes place.

According to a specific embodiment of the process of the invention, the aforementioned epoxidation of the compounds of formula I (bf) can be carried out by means of a mixture comprising an organic nitrile and hydrogen peroxide at a pH of about 8.

Typically, the organic nitrile is benzonitrile and the reaction is carried out in a solution able to keep the pH value at approximately 8. To this end an aqueous solution of sodium or potassium hydrogenocarbonate is preferred [seee.g.: J. Org. Chem., 26, 659 (1961) and Tetrahedron, 18, 763 (1962)].

The organic peracids, used to promote the epoxidation of the exocyclic double bond of the compounds of formula I (bf), can be prepared in situ by treating an organic acid, in the presence of small amounts of a mineral acid, with hydrogen peroxide according to a technique known in the art [see: H. O. House, Modern Synthetic Reactions, Benjamin, Inc., New York (1965), p. 105 and ff.].

According to the process of the present invention the compounds of formula I (ah) are obtained by catalytically hydrogenating a compound of formula I (bh). The catalysts commonly used for reducing an ethylenic double bond may be conveniently employed to this end [see: H. O. House, cited reference, pp. 1-22].

In accordance with the process of the present invention the compounds of formula I (bi) and I (ai) are obtained by reducing the carbonyl function of the compounds of formula I (bh) and I (ah), respectively. The reducing agents commonly known to promote the conversion of ketonic or aldehydic derivatives to secondary or primary alcohols, respectively, may be advantageously used [cf.: H. O. House, cited reference, pp. 23 and ff.]. Sodium boron hydride is preferred.

A further object of the process of the present invention is to prepare the esters of formula I (bi') and I (ai') by esterifying according to the usual synthetic procedures the alcohols of formula I (bi) and I (ai), respectively. This esterification can be carried out by means of common esterifying agents, such as e.g. acyl halides or anhydrides, in the presence of an organic base, preferably a tertiary organic nitrogen base [cf. e.g.: L. F. Fieser and M. Fieser, Organic Chemistry, Reinhold Publ. Corp., New York, (1956), p.174].

The process of the present invention relates further to the preparation of a ketone of formula I (de), which compound is obtained by epoxidizing a compound of formula I (be) and successively treating the obtained epoxide compounds with an acidic or basic agent.

The above preparation may be represented by the following scheme:

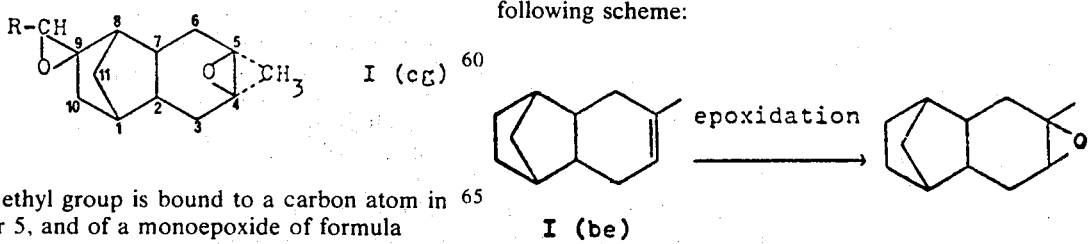

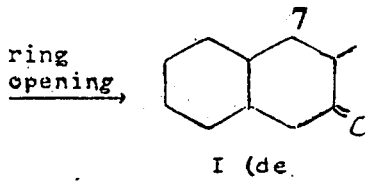

I (de)

The reaction conditions under which the compounds of formula I (bf) are converted to compounds I (bg) may be conveniently used for carrying out the hereinabove mentioned preparation. The subsequent ring-opening of the epoxide intermediate can be carried out by means of an acidic or basic agent. A suitable class of acidic agents includes a protic mineral or organic acid, or a Lewis acid, such as e.g. $BF_3$, $SnCl_4$, $FeCl_3$ or $AlCl_3$. Boron trifluoride in diethyl ether solution is preferred.

Specific examples of the compounds defined by the various formulae indicated throughout this specification include the following new compounds:

4-methyl-5-oxo-tricyclo[6.2.1.0$^{2,7}$]undecane,
4-methyl-tricyclo[6.2.1.0$^{2,7}$]undec-4-ene,
9-ethylidene-4-methyl-tricyclo[6.2.1.0$^{2,7}$]undec-4-ene,
9-ethylidene-5-methyl-tricyclo[6.2.1.0$^{2,7}$]undec-4-ene,
9-[9,12-epoxy-ethyl]-4-methyl-tricyclo[6.2.1.0$^{2,7}$]undec-4-ene,
9-[9,12-epoxy-ethyl]-5-methyl-tricyclo[6.2.1.0$^{2,7}$]undec-4-ene,
9-acetyl-4-methyl-tricyclo[6.2.1.0$^{2,7}$]undec-4-ene,
9-acetyl-5-methyl-tricyclo[6.2.1.0$^{2,7}$]undecane,
9-[1-hydroxy-ethyl]-4-methyl-tricyclo[6.2.1.0$^{2,7}$]undec-4-ene,
9-[1-hydroxy-ethyl]-5-methyl-tricyclo[6.2.1.0$^{2,7}$]undec-4-ene,
9-[1-acetoxy-ethyl]-4-methyl-tricyclo[6.2.1.0$^{2,7}$]undec-4-ene,
9-[1-acetoxy-ethyl]-5-methyl-tricyclo[6.2.1.0$^{2,7}$]undec-4-ene,
9-[1-formoxy-ethyl]-4-methyl-tricyclo[6.2.1.0$^{2,7}$]undec-4-ene,
9-[1-formoxy-ethyl]-5-methyl-tricyclo[6.2.1.0$^{2,7}$]undec-4-ene,
9-vinyl-4-methyl-tricyclo[6.2.1.0$^{2,7}$]undec-4-ene,
9-vinyl-5-methyl-tricyclo[6.2.1.0$^{2,7}$]undec-4-ene,
9-[12,13-epoxy-ethyl]-4-methyl-tricyclo[6.2.1.0$^{2,7}$]-4,5-epoxy-undecane,
9-[12,13-epoxy-ethyl]-5-methyl-tricyclo[6.2.1.0$^{2,7}$]-4,5-epoxy-undecane.

The compounds prepared in accordance with the process of the present invention occur in the form of various stereoisomers. For instance, due to the presence of an alkyl and an epoxide group, and of two hydrogen atoms in position 2 and 7 of the molecule, the compounds of formula I (bg) may be more suitably represented by the following general formula

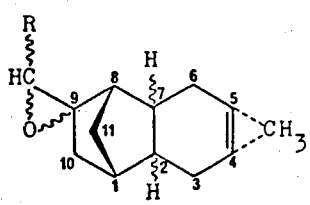

The various isomers may be separated from each other by the conventional technique of purification, for example preparative vapour phase chromatography, fractional distillation, preferably by means of spinning band columns, or fractional cristallization. However, in consideration of the fact that the organoleptic properties of the various isomers do not differ from each other significantly, the mixtures of isomers can be used as directly obtained by the process of the invention.

The compounds of formula I possess interesting organoleptic properties and, accordingly, may be used as flavouring ingredients for modifying, enhancing or improving the organoleptic properties of foodstuffs, animal feeds, beverages, pharmaceutical preparations and tobacco products, for the preparation of artificial flavouring compositions, and for the preparation of perfumes and perfumed products. The term "foodstuff" is used broadly and includes, for example, coffee, tea or chocolate. The compounds of formula I may be used as perfuming ingredients in diluted or concentrated perfume compositions. Due to their stability, particularly in basic media, these compounds may be used for masking, modifying or improving the olfactive properties of materials such as e.g. soaps, cleaning products, detergents, house-hold materials and cosmetics.

The compounds of formula I are equally useful as ingredients for the preparation of artificial essential oils, floral essential oils for example.

In perfume compositions, the compounds of the invention may develop a variety of notes, particularly woody, green or fruity notes, depending upon the nature of the composition.

Interesting effects can be obtained when the compounds of formula I constitute from 0.5 to 5 % by weight of the total composition; but, depending upon the effect required, the proportion of the compounds I may be increased to 10 % by weight, or even more.

When the compounds of formula I are used as flavouring ingredients, they can equally develop or enhance various flavouring notes, particularly fruity and green notes. They can in particular develop a fruity taste, reminiscent of citrus fruits, specifically grapefruit. The concentrations of the compounds I used for flavouring purposes can vary widely.

Typically, interesting flavouring effects can be achieved with amounts ranging from 5 to 10 ppm, based on the weight of the product flavoured. However, in order to achieve special effects, this amount can be raised to about 100 ppm. When the compounds I are used in flavouring compositions, in admixture with other flavouring agents, they may typically comprise from 0.1 % to 15 % of the total weight of the composition; and, in many cases, amounts from 1 % to 10 % by weight will give the best results.

In all cases, the ranges mentioned above may be varied, in order to achieve specific organoleptic effects.

In particular, the compounds of formula I include the 9-[9,12-epoxy-ethyl]-4- and 9-[9,12-epoxy-ethyl]-5-methyl-tricyclo[6.2.1.0$^{2,7}$]undec-4-ene, and the 5-methyl-4-oxo-tricyclo[6.2.1.0$^{2,7}$]undecane. This letter particularly develops the floral character of the composition to which it is incorporated, and possesses moverover a reinforcing and fixing power.

On the other hand, the hereinabove mentioned epoxides possess a typical woody and fruity note reminiscent of grapefruit.

The invention is illustrated by the following Examples, in which all temperatures are given in degrees centigrade.

EXAMPLE 1

9-Ethylidene-4-methyl- and 9-ethylidene-5-methyl-tricyclo [6.2.1.0$^{2,7}$]undec-4-ene A mixture of ethylidene norbornene (1500 g; 12.5 M), isoprene (900 g; 13.2 M), hydroquinone (1 g) and pyrogallol (1 g) was heated in a stainless steel autoclave at 160°–170° during 15 hours at a pressure of ca. 20 atm.

The reaction mixture was then directly distilled by means of a Vigreux column. There were thus obtained 1175 g of the desired product; b.p. 55°–60°/0.001 Torr; yield 50 %.

On separation by preparative vapour phase chromatography the endo and exo pure isomers were obtained in a proportion of approximately 80 and 20, respectively.

NMR: 1.67 (6H, s); 1.3–2.4 (12H); 5.15 (1H, m); 5.4 (1H, m) δ ppm;

MS: M$^+$ = 188 (58); m/e: 173 (6); 159 (7.5); 145 (6); 132 (20.5); 119 (14); 105 (26.5); 94 (60); 93 (100); 79 (43); 67 (21); 53 (8.5); 41 (18).

The analytical data given above refer to the mixture as directly obtained in accordance with the described process.

EXAMPLE 2

9-[9,12-Epoxy-ethyl]-4-methyl- and 9-[9,12-Epoxy-ethyl]-5-methyl-tricyclo[6.2.1.0$^{2,7}$]- undec-4-ene 1128 g (6 M) of the product prepared in accordance with the method described in Example 1, were put into a 10 l flask equipped with mecanical stirrer, thermometer and a dropping funnel stoppered by means of a calcium chloride tube, together with 485 g of sodium acetate and 3000 ml or methylene chloride. The whole was kept under vigorous stirring at a temperature of ca. −5°, whereupon 1150 g (6 M) of a 40 % aqueous peracetic acid solution and 15 g of sodium acetate, were added during 4 hours. The addition rate was such as to keep the temperature below 0°. Once the addition was finished, the reaction mixture was kept at room temperature during ca. 3 hours, then filtered. The clear filtrate thus obtained was washed with water, then with a 10 % aqueous solution of sodium carbonate and finally with two fractions of 1000 ml of water. The organic extracts separated and combined were then evaporated under reduced pressure to yield a residue which upon distillation by means of a fractionating column of the Fischer type yielded 735 g (yield 60 %) of the desired product. B.p. 75°–80°/0.001 Torr.

NMR: 1.2 (3H,m); 1.66 (3H, s); 1.3–2.3 (12H); 2.8 (1H, m); 5.4 (1H, m) δ ppm

IR : 3035, 1665 and 870 cm$^{-1}$.

By the same distillation it was possible to obtain 210 g of a diepoxide derivative having b.p. 80°–95°/0.001 Torr to which the following structural formula was attributed:

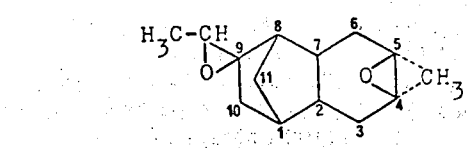

EXAMPLE 3

9-Acetyl-4-methyl- and 9-acetyl-5-methyl-tricyclo[6.2.1.0$^{2,7}$]undec-4-ene A mixture of 27.2 g (0.2 M) of 2-acetyl-bicyclo[2.2.1]hept-5-ene endo, 13.6 g (0.2 M) of isoprene, 0.1 g of pyrogallol and 0.1 g of hydroquinone were heated in a sealed tube at ca. 160° during 15 hours. There was thus obtained an inside pressure of 15 atm.

The reaction mixture was then directly distilled by means of a Vigreux column and yielded the desired product possessing the endo isomeric structure with a yield of 22 % (9.0 g); b.p. 82°–4°/0.001 Torr.

IR : 3030, 1712 cm$^{-1}$

NMR : 1.62 (3H, s); 2.03 (3H, d); 1.2–2.5 (12H); 2.75 (1H, m); 5.4 (8/10H, d); 5.85 (2/10H, t) δ ppm SM : M$^+$ = 204 (8.5); m/e: 186 (4); 171 (5); 157 (5); 146 (100); 131 (41); 117 (10); 105 (29); 91 (29); 79 (19); 66 (41.5); 55 (12.5); 43 (46.5).

By replacing the endo-2-acetyl-bicyclo[2.2.1]hept-5-ene by the corresponding exo isomer, there is obtained the desired product with the exo structure with a yield of 30 % (12.2 g).

IR : 3035 and 1710 cm$^{-1}$

NMR : 1.65 (3H, s); 2.03 (3H, s); 1.2–2.7 (13H); 5.4 (1H, m) δ ppm

MS : M$^+$ = 204 (49); m/e: 186 (2.3); 171 (2.8); 161 (39); 146 (88); 133 (44.5); 119 (24); 105 (41.5); 93 (52.5); 81 (62); 66 (74.5); 55 (17); 43 (100).

The endo-2-acetyl-bicyclo[2.2.1]hept-5-ene used as starting material for the preparation indicated above can be obtained as follows:

A solution of 132 g (2 M) of cyclopentadiene in 150 ml of anhydrous diethyl ether was rapidly added to a solution previously cooled at ca. 0° of methyl vinyl ketone (125 g; 1.78 M) in 150 ml of anhydrous diethyl ether kept under vigorous stirring. The reaction mixture was then gradually heated to room temperature, then to reflux. After 15 hours of this treatment the solution was evaporated and the obtained residue distilled by means of a Vigreux column. A mixture of the endo and exo isomers of 2-acetyl-bicyclo[2.2.1]hept-5-ene, in a ratio of 75 : 25, was thus obtained; b.p. 69°–72°/7° Torr.

The two isomers have been separated from each other by means of a distillation using a fractionating column of the Fischer type or occasionally a spinning band column.

endo: IR : 3060 and 1705 cm$^{-1}$

NMR : 1.2–1.8 (4H); 2.01 (3H, s); 2.8 (2H, m); 3.15 (1H, m); 5.72 (1H, d of d, J=5 cps, J$^1$=3 cps); 5.97 (1H, d of d) δ ppm MS : M$^+$ = 136 (9.5); m/e: 93 (12); 77 (8); 71 (16.5); 66 (100); 58 (8); 43 (23)

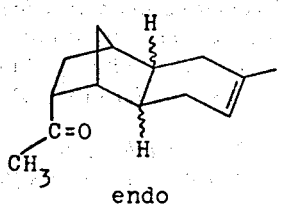

endo

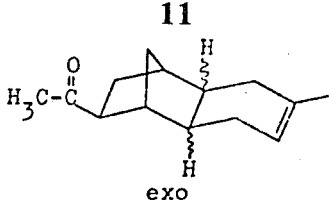

exo exo: IR : 3065 and 1710 cm$^{-1}$

NMR : 1.2-2.5 (5H); 2.12 (3H, s); 2.9 (2H, m); 6.05 (2H, t, J=2 cps) δ ppm

MS : M$^+$ = 136 (14); m/e: 93 (13); 77 (12); 71 (26.5); 66 (100); 55 (5); 43 (24).

EXAMPLE 4

9-Vinyl-4-methyl- and 9-vinyl-5-methyl-tricyclo[6.2.1.0$^{2,7}$]undec-4-ene

A mixture of 120 g (1 M) of vinyl norbornene, 68 g of isoprene (1 M) and 0.2 g of hydroquinone was heated in a sealed tube at ca. 165° during 15 hours, whereupon an internal pressure of 15 atm. was reached.

The reaction mixture was then distilled by means of a Vigreux column to yield the desired product having b.p. 65°–70°/0.001 Torr; 65.5 g (yield 35 %).

IR : 3095, 3035 and 1636 cm$^{-1}$

NMR : 1.65 (3H, s); 1.2-2.8 (13H); 4.8 (2H, m); 5.4 (1H, m); 5.8 (1H, m) δ ppm

MS : M$^+$ = 188 (31); m/e: 173 (5.5); 159 (3); 146 (13); 134 (32); 119 (26.5); 105 (28.5); 91 (39); 79 (38); 66 (100); 53 (8.5); 41 (21).

The product thus obtained was subjected to an epoxidation according to the same procedure as that described for the preparation of 9-]9,12-epoxy-ethyl]-4-methyl- and 9-]9,12-epoxy-ethyl]-5-methyl-tricyclo[6.2.1.0$^{2,7}$]undec-4-ene (cf. Example 2) by using the following ingredients in the given quantities:

| | |
|---|---|
| 9-vinyl-4-methyl- and 9-vinyl-5-methyl-tricyclo [6.2.1.0$^{2,7}$]undec-4-ene | 65 g (0.35 M) |
| peracetic acid 40 % | 71 g (0.37 M) |
| anhydrous sodium acetate | 28.5 g (0.35 M) |
| methylene chloride | 300 ml |

On distillation by means of a Widmer column there were obtained 57.6 g of 9-vinyl-4-methyl- and 9-vinyl-5-methyl-tricyclo[6.2.1.0$^{2,7}$]-4,5-epoxy-undecane, b.p. 67°–8°/0.001 Torr; and 10.0 g of 9-[12,13-epoxy-ethyl]-4-methyl- and 9-[12,13-epoxy-ethyl]-5-methyl-tricyclo[6.2.1.0$^{2,7}$]-4,5-epoxy-undecane, b.p. 68°–87°/0.001 Torr.

IR : 3090 and 1635 cm$^{-1}$

NMR : 1.18 (3H, s); 1.3-2.3 (13H); 2.72 (1H, d); 4.8 (2H); 5.65 (1H, m) δ ppm

MS : M$^+$ = 204 (29); m/e: 189 (11.5); 175 (22.5); 162 (25); 148 (35); 131 (25); 117 (29); 105 (35); 91 (69); 79 (75); 66 (54); 55 (29); 43 (100).

By using 2.2 equivalents of peracetic acid for 1 equivalent of starting material there is obtained the diepoxide derivative (see Ex. 2) with a yield of 80 %.

NMR : 1.2 (3H, s); 1.3-2.1 (13H); 2.2-2.9 (4H, m) δ ppm

MS : M$^+$ = 220 (6); m/e: 205 (4); 189 (18); 148 (35); 131 (21); 91 (30); 79 (57); 66 (34); 55 (29); 43 (100).

EXAMPLE 5 endo-9-[1-Acetoxy-ethyl]-4-methyl- and endo-9-[1-Acetoxy-ethyl]-5-methyl-tricyclo[6.2.1.0$^{2,7}$]undec-4-ene a. 9-[1-Hydroxy-ethyl]-4-methyl- and 9-[1-hydroxyethyl]-5-methyl-tricyclo[6.2.1.0$^{2,7}$]undec-4-ene A solution of 0.7 g (0.018 M) of sodium boron hydride in 7 ml of water was added dropwise under vigorous stirring to a solution of 7.3 g (0.036 M) of 9-acetyl-4-methyl- and 9-acetyl-5-methyl-tricyclo[6.2.1.0$^{2,7}$]undec-4-ene, prepared according to the procedure described in Example 3, in 50 ml of methanol. The reaction mixture was kept at a temperature comprised between about 30° and 40° during the whole addition, whereupon it was heated at reflux during 2 hours. The volatile portions were then evaporated and the residue extracted twice with diethyl ether. The combined organic extracts were washed with a 36 % solution of NaOH, then with water until neutrality. After drying over MgSO$_4$ and evaporation the obtained residue was distilled. There were thus obtained 6.4 g (87 %) of the desired product having b.p. 100-103°/0.001 Torr.

IR : 3400 cm$^{-1}$

NMR : 1.12 (3H, d); 1.67 (3H, s); 1.4-2.5 (13H); 2.5-3.6 (1H); 3.9 (1H, s); 5.4 (2/3H); 5.9 (1/3H) δ ppm MS : M$^+$ = 206 (12); m/e: 188 (5); 173 (4); 159 (7.5); 145 (11); 132 (22.5); 117 (9.5); 105 (14); 91 (21); 79 (26); 66 (100); 55 (7.5); 41 (14).

b. Acetylation of the product obtained according to (a)

A mixture of 4.1 g (0.02 M) of the hydroxylic compound obtained according to a), 4.1 g of acetic anhydride (0.04 M) and 4.1 g of anhydrous pyridine was heated during 2 hours on a water bath, then it was poured onto crushed ice and extracted twice with diethyl ether. The ether extracts were combined and washed with a 10 % aqueous solution of HCl (4 times), then with an aqueous solution of sodium carbonate (twice) and finally with water until neutrality. After drying on MgSO$_4$ the volatile portions were evaporated and the residue obtained was distilled through a Vigreux column. There were thus obtained 4.1 g of the desired product (yield 83 %); b.p. 90°–94°/0.005 Torr.

IR : 1730 cm$^{-1}$

NMR : 1.1 (3H, d); 1.66 (3H, s); 1.95 (3H, s); 1.3-2.8 (13H); 4.7 (1H, s); 5.4 (2/3H); 5.9 (1/3H) δ ppm MS : M$^+$ = 248 (8); m/e: 188 (25); 173 (7); 159 (8); 145 (23); 132 (33); 121 (23); 105 (21); 93 (35); 79 (30); 66 (100); 55 (23); 43 (65).

The procedure indicated hereinabove can equally be applied to the exo isomer of 9-acetyl-4-methyl- and 9-acetyl-5-methyl-tricyclo[6.2.1.0$^{2,7}$]undec-4-ene to yield the corresponding acetoxy derivative in the exo form.

exo:

IR : 1735 cm$^{-1}$

NMR : 1.1 (3H, m); 1.65 (3H, s); 1.95 (3H); 4.5 (1H); 5.35 (2/3H); 5.9 (1/3H) δ ppm MS : M$^+$ = 248 (12); m/e: 188 (20); 173 (4.5); 159 (6.5); 145 (8.5); 132 (14.5); 121 (16); 105 (19); 94 (46.5); 79 (32); 66 (100); 55 (23); 43 (70).

EXAMPLE 6

Exo- and endo-9-acetyl-4-methyl- and 9-acetyl-5-methyl-tricyclo[6.2.1.0$^{2,7}$]undecane 2.04 g (0.010 M) of endo-9-acetyl-4-methyl- and 9-acetyl-5-methyl-tricyclo[6.2.1.0$^{2,7}$]undec-4-ene in 20 ml of ethanol were subjected to a hydrogenation in the presence of 50 mg of PtO$_2$. After absorption of the theoretical amount of hydrogen (30 minutes), the reaction mixture was filtered and the clear filtrate evaporated until complete elimination of ethyl alcohol. The residue thus obtained was purified by passing it through a column of SiO$_2$ (70 g) by using as an eluant a mixture (95 : 5) of hexane and ether. After evaporation of the volatile portions the desired product, the endo isomer, was obtained by distillation using a bulb distillation apparatus; b.p. 60°/0.001 Torr; 405 mg (yield 20 %).

IR : 1710 cm$^{-1}$

NMR : 0.9 (3H, d); 2.05 (3H, s); 1.2-2.5 (15H); 2.75 (1H, m) δ ppm

MS : M$^+$ = 206 (0.1); m/e: 188 (0.2); 173 (0.4); 163 (6); 148 (100); 135 (34); 119 (3.5); 106 (9); 93 (12); 81 (15); 67 (19); 55 (15); 43 (32).

By carrying out the hydrogenation according to the same procedure as given above on the exo isomer of 9-acetyl-5-methyl- and 9-acetyl-4-methyl-tricyclo[6.2.1.0$^{2,7}$]undec-4-ene there is obtained the corresponding exo-undecane derivative with a yield of 24 %.

Exo-9-acetyl-4-methyl- and exo-9-acetyl-5-methyl-tricyclo [6.2.1.0$^{2,7}$]undecane:
IR : 1710 cm$^{-1}$ NMR : 0.9 (3H); 2.06 (3H, s); 1.2-2.1 (15H); 2.35 (1H, m) δ ppm MS : M$^+$ = 206 (0); m/e: 188 (0.2); 163 (72); 148 (100); 135 (29.5); 121 (14); 107 (22.5); 95 (36.5); 81 (79); 67 (79); 55 (49); 43 (39).

Example 7

9-[1-Formoxy-ethyl]-4-methyl- and 9-[1-formoxy-ethyl]-5-methyltricyclo[6.2.1.0$^{2,7}$]undec-4-ene A mixture of the hydroxylic compound obtained in accordance with the procedure described in paragraph (a) of Example 5 (10.3 g; 0.05 M) and 23 g of 98 % formic acid (0.5 M) was heated during 2 hours at 40°. After cooling the reaction mixture was extracted twice with diethyl ether. The combined organic extracts were washed three times with an aqueous saturated solution of sodium bicarbonate (10 ml) and then with water until neutrality. After drying over magnesium sulphate, the extracts were evaporated under reduced pressure to yield a residue which, by fractional distillation, gave a product having b.p. 70°-1°/0.001 Torr; 8.6 g (yield 73.5 %).

On purification by means of preparative vapour phase chromatography (CARBOWAX 20 M, column; 2.5 m; 220°) there are obtained the two pure endo and exo isomers of the desired product:

A : IR : 1720 and 1180 cm$^{-1}$

NMR : 1.2 (3H, d); 1.65 (3H, s); 4.8 (1H, m); 5.2 (1H, s); 7.92 (1H, s) δ ppm

MS : M$^+$ = 234; m/e: 188 (50); 173 (24.5); 159 (26); 145 (20.5); 132 (100); 117 (16); 105 (25); 95 (44.5); 79 (44.5); 67 (12); 55 (10.5); 41 (16).

B : IR : 1725 and 1185 cm$^{-1}$

NMR : 1.15 (3H, d); 1.65 (3H, s); 4.7 (1H, m); 5.25 (1H, m); 7.95 (1H, s) δ ppm

MS : M$^+$ = 234; m/e: 188 (11.5); 173 (4); 159 (8); 145 (29); 132 (18.5); 122 (16); 105 (9.5); 91 (19); 79 (23); 66 (100); 55 (7); 41 (7).

EXAMPLE 8

5-Methyl-4-oxo-tricyclo[6.2.1.0$^{2,7}$]undecane a. A mixture of 715 g (7.6 M) of norbornene, 550 g (8.1 M) of isoprene and 2 g of pyrogallol was heated in a stainless steel autoclave at ca. 150° during 15 hours. An internal pressure of 20 atm. is thus reached. The reaction mixture was then distilled by means of a Vigreux column and yielded 467 g (yield 38 %) of 5-methyl-tricyclo[6.2.1.0$^{2,7}$]undec-4-ene having b.p. 90°/10 Torr.

MS : M$^+$ = 162 (66); m/e: 147 (19); 134 (33); 119 (19); 105 (23) 94 (57); 79 (64); 66 (100); 53 (20); 41 (35); 27 (15).

NMR (CCl$_4$) : 0.9-1.8 (10H); 1.67 (3H, s); 1.90 (4H, m); 5.42 (1H, d, J=6.7 cps) δ ppm.

b. 24.3 g (0.15 M) of the product prepared according to a), 31 g of anhydrous sodium acetate and 150 ml of methylene chloride were poured into a flask equipped with mechanical stirrer, thermometer and a dropping funnel stoppered with a calcium chloride tube. The whole was kept under vigorous stirring at ca. 0°, whereupon there is added during 15 minutes a 40 % solution of peracetic acid (29 g; 0.15 M) and 1 g of anhydrous sodium acetate. The addition rate was such as to keep the temperature comprised between about 0° and 5°. Once the peracetic acid addition was over, the reaction mixture was kept at room temperature during 3 hours, then filtered. The clear filtrate obtained was washed with water, then twice with a 10 % aqueous solution of sodium carbonate (100 ml each) and finally with water again. The organic layers were then evaporated under reduced pressure to yield a residue which on distillation through a Vigreux column yielded 25.8 g of 5-methyl-4,5-epoxy-tricyclo[6.2.1.0$^{2,7}$]undecane (yield 97 %), b.p. 110°/10 Torr. MS : M$^+$ = 178 (35); m/e: 163 (30); 149 (40); 136 (21); 120 (9); 111 (48); 92 (52); 79 (50); 67 (61); 55 (24); 43 (100); 27 (21)

NMR (CCl$_4$) : 1.18 (3H, s); 2.73 (1H, d, J=3.9 cps) δ ppm.

c. 12.7 g (0.07 M) of the epoxide compound prepared in accordance with paragraph b) in 300 ml of dry toluene were poured into a flask equipped with mechanical stirrer, thermometer and dropping funnel. To the reaction mixture kept at 20° there were then added during 30 minutes 19.8 g (0.14 M) of trifluoroboroetherate, then 50 ml of a 5 % aqueous solution of sodium bicarbonate. The solution which had acquired a brownish colour after the addition of the trifluoroboroetherate became colourless. It was then washed with a 5 % aqueous solution of sodium bicarbonate (100 ml) and with water (twice, 100 ml). The organic layer was dried over anhydrous magnesium sulphate and evaporated under reduced pressure. By fractional distillation of the residue there are obtained 10.8 g of 5-methyl-4-oxo-tricyclo[6.2.1.0$^{2,7}$]undecane, b.p. 120°-2°/10 Torr (yield 85 %).

MS : M$^+$ = 178 (78); m/e: 163 (3); 150 (70); 136 (100); 121 (23); 109 (43); 93 (39); 79 (66); 67 (91); 55 (37); 41 (64); 27 (27).

NMR (CCl$_4$) : 1.08 (3H, d, J=7.5 cps) δ ppm

IR (CCl$_4$) : 1710 cm$^{-1}$.

EXAMPLE 9

Perfume composition of the "Gardenia" type

A base perfume composition of the "Gardenia" type was prepared by admixing the following ingredients (parts by weight):

| | |
|---|---|
| Phenylacetic aldehyde 10 %* | 30 |
| Benzyl acetate | 50 |
| Synth. jasmin | 250 |
| Ylang | 60 |
| Lynalyl acetate | 90 |
| Methyl anthranilate | 30 |
| β-Methylnaphtyl ketone | 30 |
| Phenylethyl alcohol | 100 |
| Hydroxycitronellal | 80 |
| Cinnamic alcohol | 70 |
| Heliotropin | 30 |
| Benzyl salicylate | 70 |
| Methyl salicylate | 10 |
| Musk ketone | 30 |
| Diethyl phthalate | 70 |
| | 1000 |

*in diethyl phthalate

By adding to 96 g of the above given base composition 4 g of 9-[9,12-epoxy-ethyl]-4-methyl-tricyclo[6.2.1.0$^{2,7}$]undec-4-ene there is obtained a perfume composition possessing a rounder character than that of the base composition and having as well floral and green notes more marked than that one.

When 9-[9,12-epoxy-ethyl]-4-methyl-tricyclo[6.2.1.0$^{2,7}$]undec-4-ene was replaced by 9-[9,12-epoxy-ethyl]-5-methyl-tricyclo[6.2.1.0$^{2,7}$]undec-4-ene or by a mixture containing the two positional isomers, analogous effects were observed.

EXAMPLE 10

Perfumed soap

A base perfume composition of the "Gardenia" type was prepared according to the same procedure as that indicated in Example 9. Said base composition was then added in the proportion of 1 % by weight, based on the finished product, to a non-perfumed commercial soap paste ("control" material).

A "test" material was prepared by admixing in the proportion of 1 % by weight, based on the finished product, a perfume composition obtained by adding to the base composition (96 parts) 4 parts by weight of a mixture consisting of 9-9,12-epoxy-ethyl]-4-methyl- and 9-[9,12-epoxy-ethyl]-5-methyl-tricyclo[6.2.1.0$^{2,7}$]undec-4-ene.

The perfumed soap pastes were treated according to the usual techniques in order to obtain toilet soaps.

The "test" soap possesses a perfume having a rounder character than that of the "control" soap and having as well more marked floral and green notes than that one.

EXAMPLE 11

Flavouring composition

A base flavouring composition was prepared by admixing one part by weight of orange terpenes with 9 parts by weight of 95 % ethyl alcohol ("control").

Two flavouring compositions were prepared separately by admixing the following ingredients (parts by weight):

| | | |
|---|---|---|
| Orange terpenes | 1.00 | 1.00 |
| 95 % Ethyl alcohol | 8.60 | 8.80 |
| Compound A* | 0.40 | 0.20 |
| | 10.00 | 10.00 |

*Compound A = 9-[9,12-epoxy-ethyl]-4-methyl-tricyclo[6.2.1.0$^{2,7}$]undec-4-ene These two compositions represent the "test" compositions.

The aromatization of a diluted acid syrup, prepared by dissolving 650 g of glucose and 10 g of a 50 % solution of citric acid in 1000 ml of water, is carried out by adding 3 g of the "test" and "control" composition to 1000 ml of the syrup prepared as indicated above. The foodstuffs thus flavoured were subjected to the organoleptic evaluation by a panel of experts. The foodstuff flavoured by the control composition was judged as having a slight orange taste, whereas the foodstuffs flavoured by the two test compositions were judged as having a more pronounced taste of grapefruit as well as a woody note.

When 9-[9,12-epoxy-ethyl]-4-methyl-tricyclo[6.2.1.0$^{2,7}$]undec-4-ene was replaced by 9-[9,12-epoxy-ethyl]-5-methyltricyclo[6.2.1.0$^{2,7}$]undec-4-ene or by a mixture of the two positional isomers, analogous effects were observed.

EXAMPLE 12

7 g of a 1 % alcoholic solution of a mixture of 9-[9,12-epoxy-ethyl]-4-methyl- and 9-[9,12-epoxy-ethyl]-5-methyl-tricyclo[6.2.1.0$^{2,7}$]undec-4-ene (in 95 % ethyl alcohol) were sprayed onto a mixture of tobacco of "american blend" type (100 g). The tobacco thus flavoured was used to manufacture test cigarettes, the smoke of which was then subjected to organoleptic evaluation by comparison with nonflavoured cigarettes (control). The tobacco used to prepare the control cigarettes was preliminarily treated with 95 % ethyl alcohol. A panel of experts unanimously defined the taste of the test cigarette as being woodier than that of the control cigarette.

EXAMPLE 13

Perfume composition of the "Lavender" type

A base perfume composition of the Lavender type was prepared by admixing the following ingredients (parts by weight):

| | |
|---|---|
| Coumarin | 50 |
| Musk ambrette | 20 |
| Lavandin oil | 100 |
| Lynalyl acetate | 300 |
| Linalol | 200 |
| Synth. bergamot | 150 |
| White thyme oil | 10 |
| Sage oil | 10 |
| Synth. geranium | 30 |
| α-Ionone | 10 |
| Allyl ionone | 20 |
| Diethyl phthalate | 100 |
| | 1000 |

By adding to the above base composition (90 parts) 10 parts by weight of 5-methyl-4-oxo-tricyclo[6.2.1.0$^{2,7}$]undecane there is obtained a perfume composition having a lavender character more pronounced than that of the base composition.

I claim:

1. A perfume composition comprising as one of its active ingredients at least one compound selected from the group consisting essentially of 9-[9,12-epoxy-ethyl]-4methyl-tricyclo[6.2.1.0$^{2,7}$]undec-4-ene and 9-[9,12-epoxy-ethyl]-5-methyl-tricylco[6.2.1.0$^{2,7}$]undec-4-ene in admixture with a suitable carrier.

* * * * *

UNITED STATES PATENT AND TRADEMARK OFFICE
CERTIFICATE OF CORRECTION

PATENT NO. : 3,979,338

DATED : September 7, 1976

INVENTOR(S) : Erling Sundt

It is certified that error appears in the above-identified patent and that said Letters Patent are hereby corrected as shown below:

In the Title Page, References Cited "Natla et al." should be --Natta et al.--

Column 6, line 17, "[seee. g.:" should be --[see e.g.:--.

Column 7, line 6, "I (de" should be --I (de)--.

Column 8, lines 61-62, "moverover" should be --moreover--.

Column 10, line 45, "72°/7° Torr" should be --72°/7 Torr--

Column 11, line 27, "1636 $cm^{-1}$" should be --1635 $cm^{-1}$--.

Column 11, line 35, "9-]9,12" should be --9-[9,12--.

Column 11, line 36, "9-]9,12" should be --9-[9,12--.

Column 15, line 45, "9-9,12" should be --9-[9,12--.

Column 15, line 50, "possesses" should be --possessed--.

Column 16, line 10, "control" should be --"control"--.

Column 16, line 12, "test" should be --"test"--.

Column 16, line 27, "test" should be --"test"--.

Column 16, line 30, "(control)" should be --("control")--.

Column 16, line 30, "control" should be --"control"--.

Column 16, line 33, "test" should be --"test"--.

UNITED STATES PATENT AND TRADEMARK OFFICE
CERTIFICATE OF CORRECTION

PATENT NO. : 3,979,338

DATED : September 7, 1976

INVENTOR(S) : Erling Sundt

It is certified that error appears in the above-identified patent and that said Letters Patent are hereby corrected as shown below:

Column 16, line 34, "control" should be --"control"--.

Column 16, line 39, "Lavender" should be --"Lavender"--.

Signed and Sealed this

First Day of March 1977

[SEAL]

Attest:

RUTH C. MASON
*Attesting Officer*

C. MARSHALL DANN
*Commissioner of Patents and Trademarks*